United States Patent [19]
Nashef et al.

[11] Patent Number: 5,682,899
[45] Date of Patent: Nov. 4, 1997

[54] APPARATUS AND METHOD FOR CONTINUOUS CARDIAC OUTPUT MONITORING

[75] Inventors: Samer Abdel-Malik Nashef, Brampton, England; Aws Salim Nashef, Huntington Beach, Calif.; Yassir Kamel Abdul-Hafiz, Fountain Valley, Calif.

[73] Assignee: AMI-MED Corporation, Irvine, Calif.

[21] Appl. No.: 21,181

[22] Filed: Feb. 23, 1993

Related U.S. Application Data

[63] Continuation-in-part of Ser. No. 701,217, May 16, 1991, abandoned.

[51] Int. Cl.$^6$ .................................................. A61B 5/02
[52] U.S. Cl. .......................... 128/692; 128/713; 128/736; 73/204.16
[58] Field of Search ............................ 128/692, 713, 128/736; 73/204.16, 204.25, 204.26, 204.27

[56] References Cited

U.S. PATENT DOCUMENTS

| | | |
|---|---|---|
| 3,359,974 | 12/1967 | Khalil . |
| 4,217,910 | 8/1980 | Khalil . |
| 4,236,527 | 12/1980 | Newbower et al. . |
| 4,240,441 | 12/1980 | Khalil . |
| 4,300,391 | 11/1981 | Eiermann .................. 703/204.27 |

(List continued on next page.)

FOREIGN PATENT DOCUMENTS

| | | |
|---|---|---|
| 0235811 | 3/1987 | European Pat. Off. . |
| 2112767 | 7/1972 | France . |
| 2411392 | 7/1979 | France . |
| WO8911083 | 11/1989 | WIPO . |
| WO9117703 | 11/1991 | WIPO . |

OTHER PUBLICATIONS

"Thermal Method for Continuous Blood–Velocity Measurements in Large Blood Vessels, and Cardiac Output Determinations", *Medical and Biological Engineering*, A. L. Delanois, Mar. 1973, pp. 201–205, vol. 11, No. 2.

"Catheterization of the Heart in Man with Use of a Flow--Directed Balloon-Tipped Catheter"; H.J.C. Swan, William Ganz, James Forrester, Harold Marcus, George Diamond and David Chonette: The New England Journal of Medicine; Aug. 27, 1970.

(List continued on next page.)

*Primary Examiner*—Kyle L. Howell
*Assistant Examiner*—Robert L. Nasser, Jr.
*Attorney, Agent, or Firm*—Knobbe, Martens, Olson & Bear

[57] ABSTRACT

A fluid volume flow monitoring apparatus, fluid volume flow monitoring system and process of monitoring fluid volume flow are disclosed. The fluid volume flow monitoring apparatus includes a support member having a distal end, a proximal end, and an outer wall with a first temperature sensing means for sensing fluid temperature positioned on the support member outer wall. A second temperature sensing means is positioned apart from the first temperature sensing means and juxtaposed to a generally tubular heat transfer device which is radially disposed about the support member outer wall. The heat transfer device directly contributes to the ability of the monitor to determine continuously fluid volume flow and includes an electrically insulated heating means positioned between a temperature equilibrator and an insulating material.

29 Claims, 10 Drawing Sheets

U.S. PATENT DOCUMENTS

| | | |
|---|---|---|
| 4,319,483 | 3/1982 | Durham, Jr. et al. . |
| 4,616,505 | 10/1986 | Jouwsma .............................. 73/204.26 |
| 4,685,470 | 8/1987 | Sekii, et al. . |
| 4,745,805 | 5/1988 | Granier ................................ 73/204.16 |
| 4,783,996 | 11/1988 | Ohta et al. . |
| 4,817,624 | 4/1989 | Newbower . |
| 4,841,981 | 6/1989 | Tanabe et al. . |
| 4,941,475 | 7/1990 | Williams et al. . |
| 4,979,514 | 12/1990 | Sekii et al. . |
| 5,003,490 | 3/1991 | Castelaz et al. . |
| 5,056,526 | 10/1991 | Khalil . |
| 5,092,343 | 3/1992 | Spitzer et al. . |
| 5,121,443 | 6/1992 | Tomlinson . |
| 5,217,019 | 6/1993 | Hughes . |
| 5,243,988 | 9/1993 | Sieben et al. . |
| 5,247,584 | 9/1993 | Krogmann . |
| 5,261,411 | 11/1993 | Hughes . |

OTHER PUBLICATIONS

"Determination of Cardiac Output in Man by a New Method Based on Thermodilution"; H.H. Khalil; Preliminary Communications, Jun. 22, 1963.

"Continuous Thermal Measurement of Cardiac Output"; James H. Philip, Michael C. Long, Michael D. Quinn and Ronald S. Newbower; IEEE Transactions on Biomedical Engineering, vol. BME-31, No. 5, May 1984.

"A Cardiac Output Estimation Algortihm for a Catheter-Based Cold-Fluid Heat Exchanger System"; Fred K. Forster, John Y.J. Yan and Royce W. Johnson; 1993 IEEE.

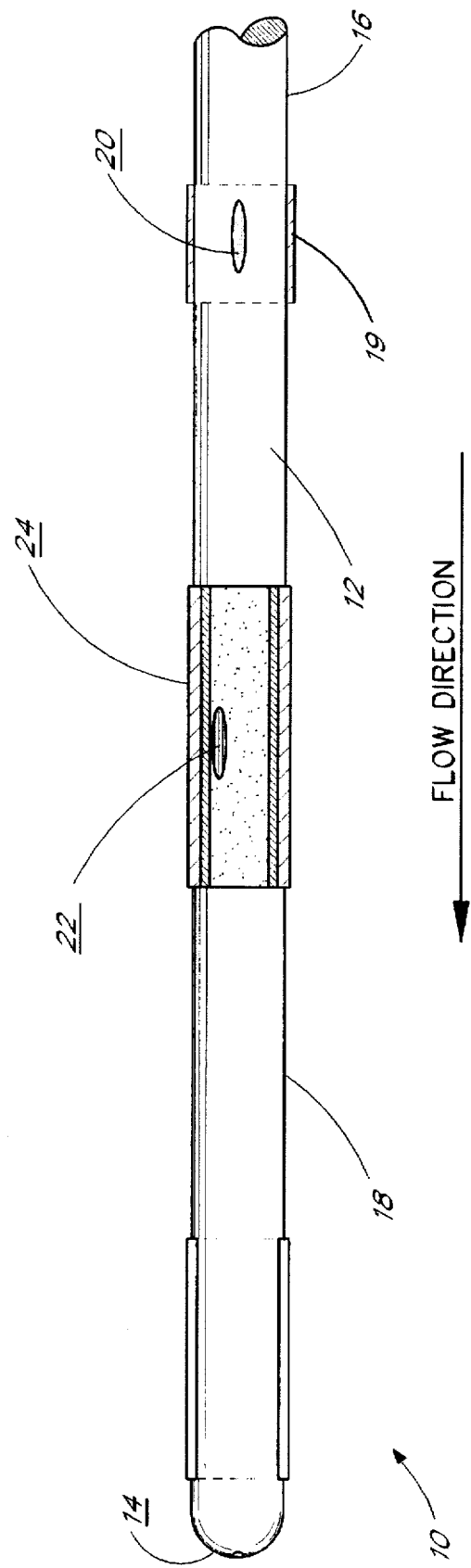

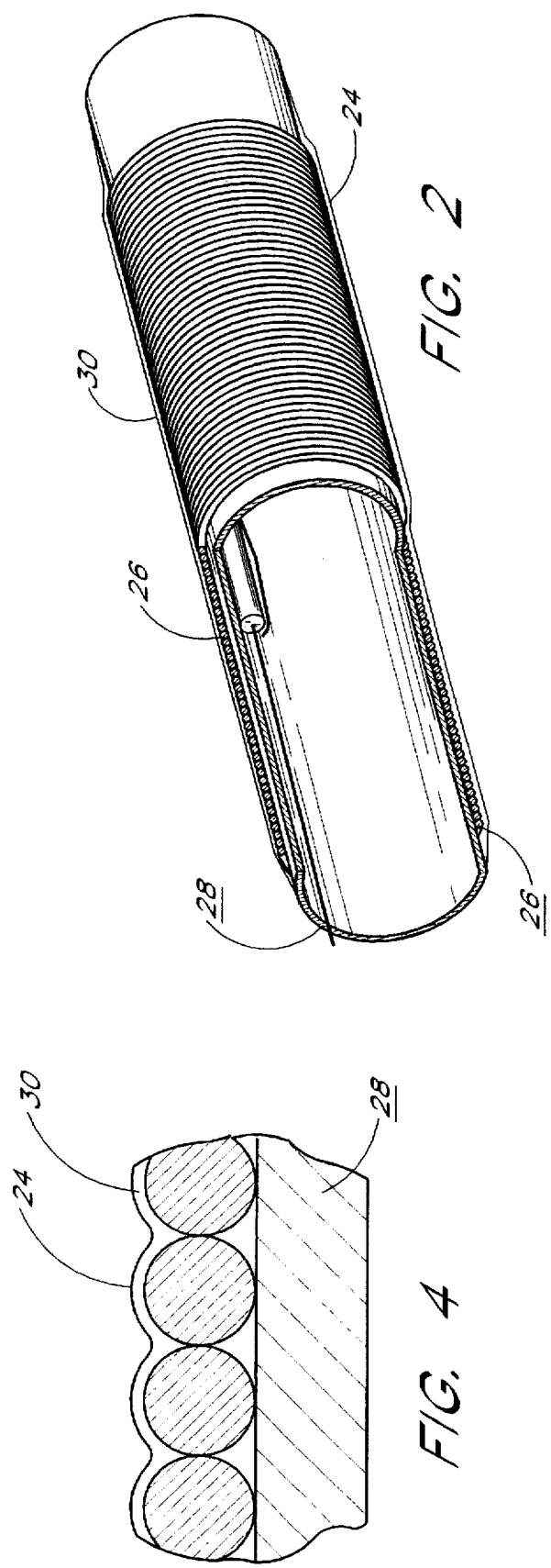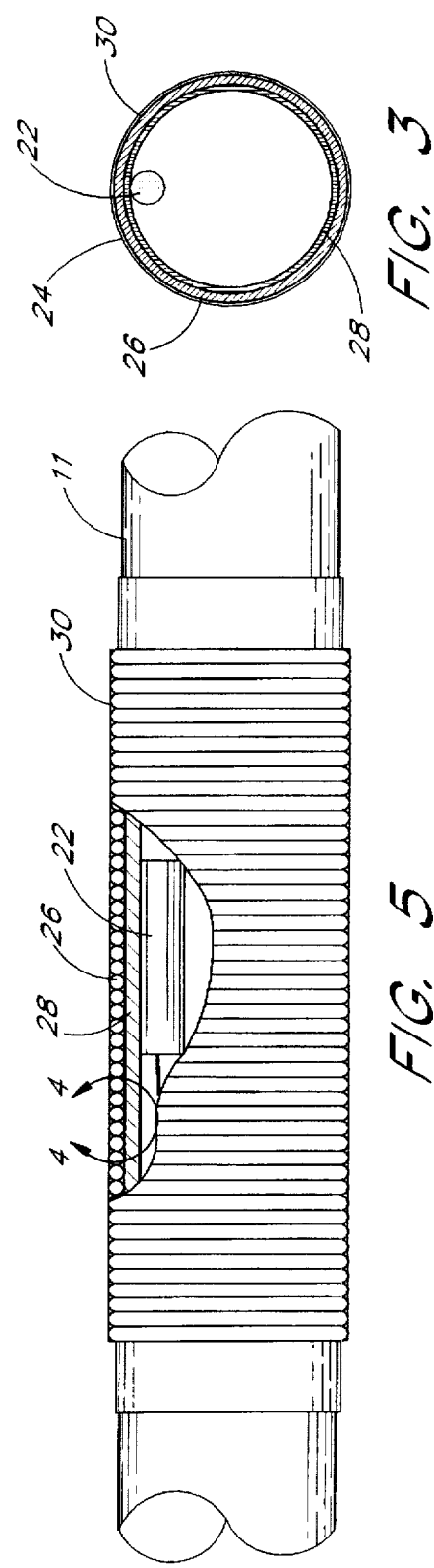

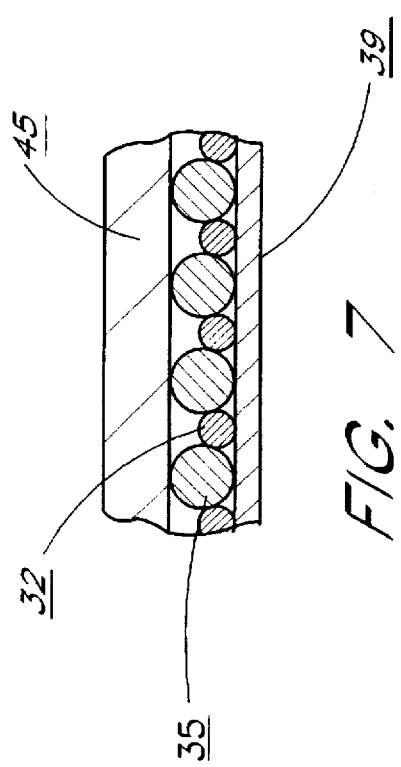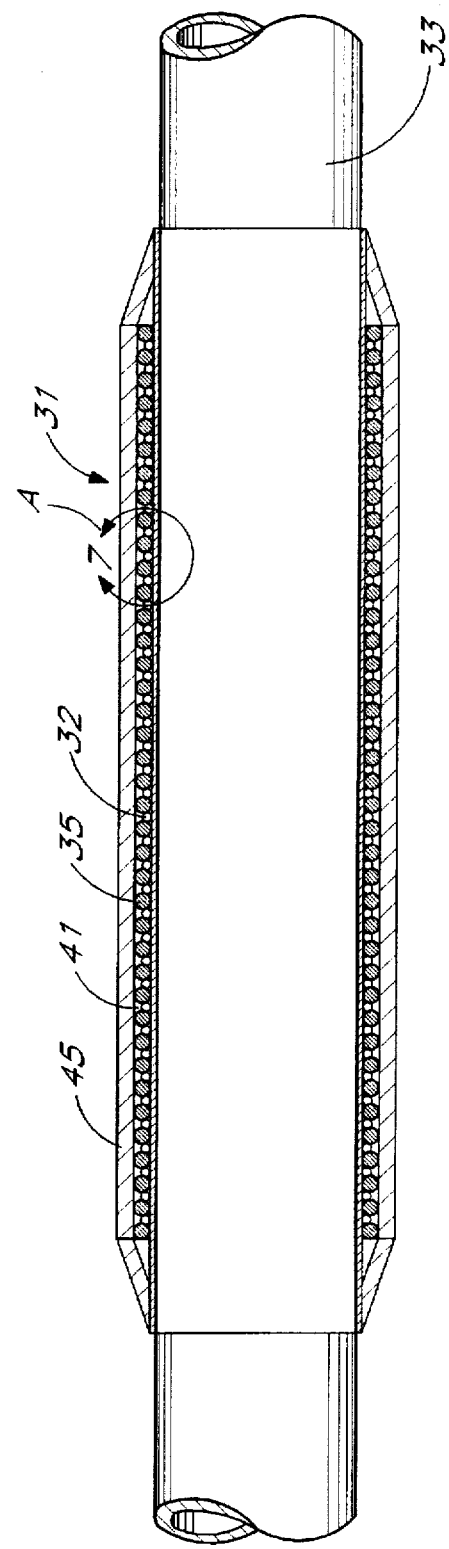

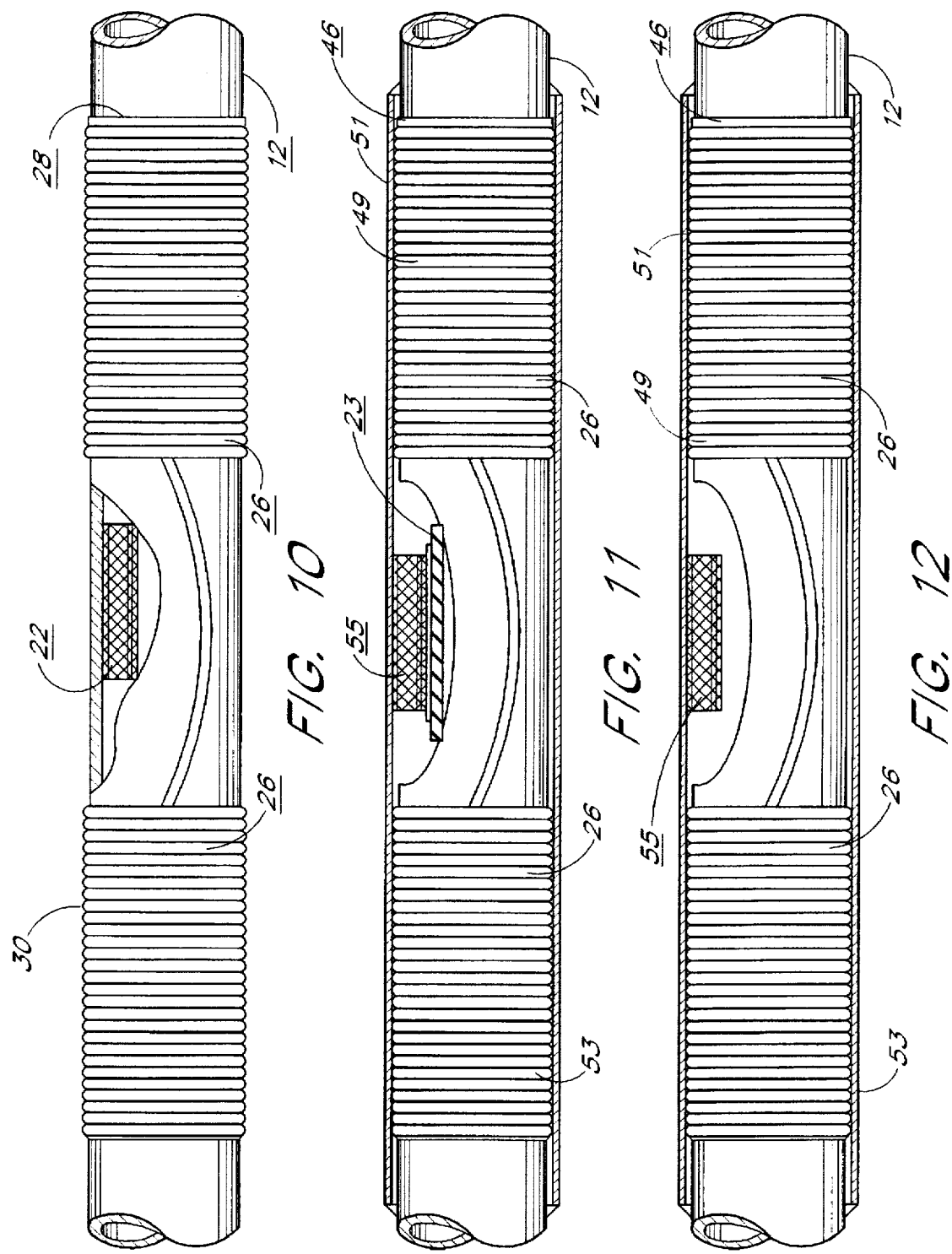

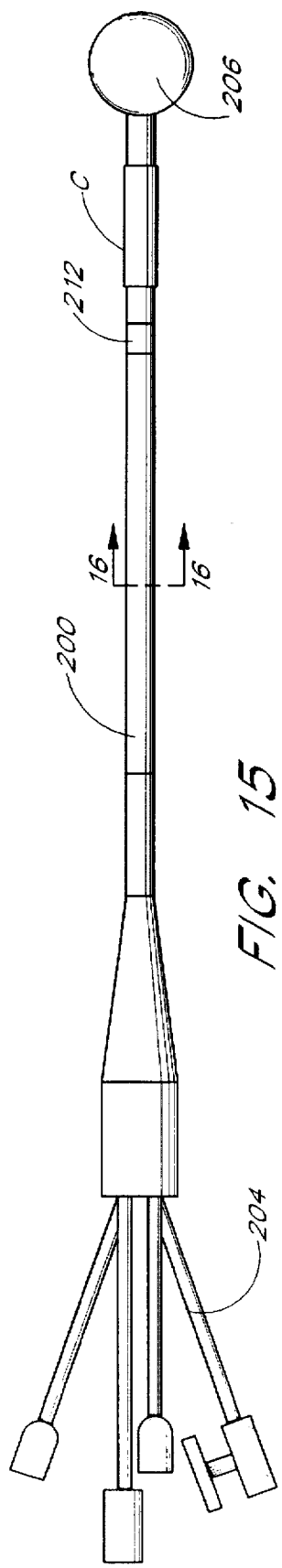
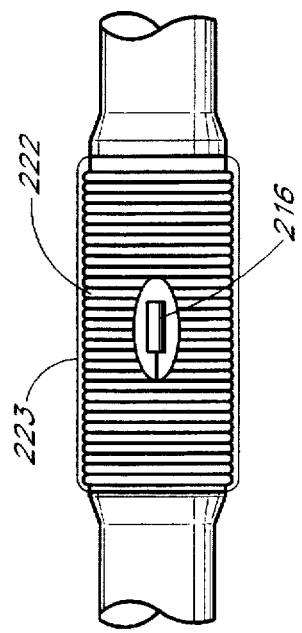
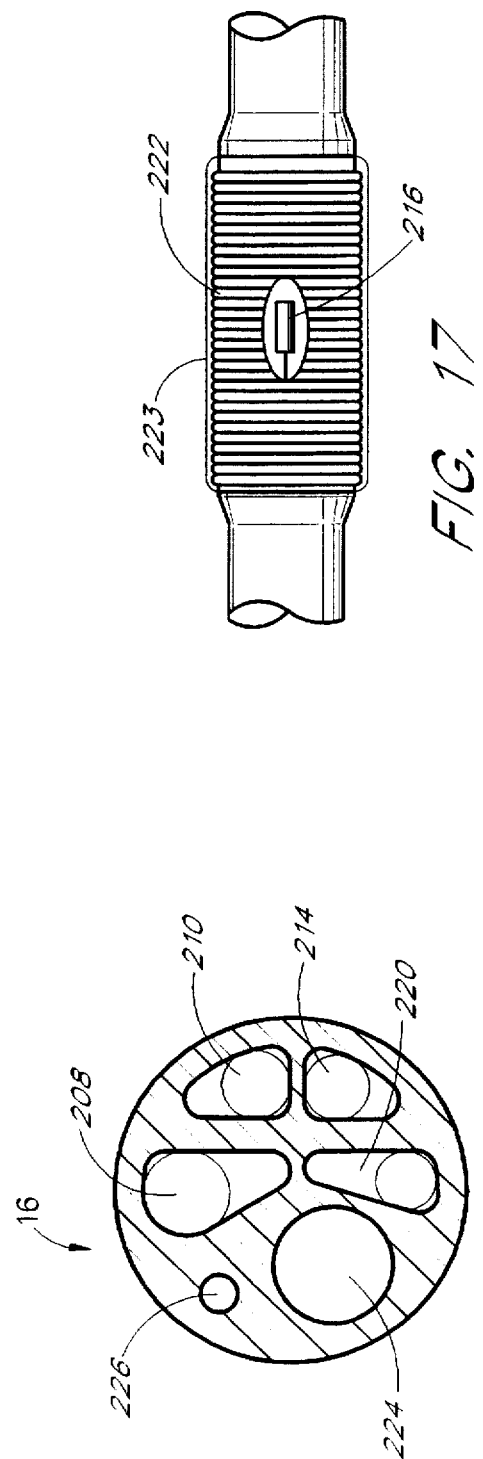

APPARATUS AND METHOD FOR CONTINUOUS CARDIAC OUTPUT MONITORING

C-I-P of application Ser. No. 07/701,217 filed May 16, 1991 now abandoned.

BACKGROUND OF THE INVENTION

1. Field of the Invention

The present invention relates in general to apparatus and methods for measuring fluid volume flow. More particularly, the present invention relates to apparatus and methods for continuously monitoring cardiac output by directly determining blood volume flow within a body cavity having flowing blood.

2. Description of Related Art

For the past two decades healthcare professionals have used cardiac output monitors as a powerful tool for monitoring blood flow in patients with a variety of medical indications. The utility of cardiac output monitors extends to applications in which an accurate determination of cardiac output in the form of blood volume flow can be of vital importance. These applications include patient pre-operative diagnosis, monitoring cardiac performance of the critically ill, post-operative monitoring, and during surgery itself. The value of cardiac output monitoring provides early warning of possible deterioration in cardiac function and can assist in the assessment of the effectiveness of therapeutic intervention to aid or stimulate an ailing heart.

There are several methods currently utilized to monitor cardiac output, each of them having their attendant advantages and disadvantages. The Fick method involves injecting a known amount of a dye into a patient's arm artery and subsequently measuring the dye concentration in the vein of the other arm. The degree of the rate of dilution in concentration of dye in the vein is assumed to be directly proportional to the patient's cardiac output. While the Fick method is attractive for its simplicity there are several problems associated with performing this method. Typically, the dye concentration measurement are performed outside the body and a single measurement can require multiple samples of blood. This is both burdensome and an annoyance to the patient. Additionally, many medical professionals prefer to avoid the presence of dye or significant amounts of dye in the blood. Thus, in limiting the amount of dye injected into the blood to keep the level of dye as low as possible, there is necessarily a limitation in the number of measurements which can be performed. Also inherent in this procedure are measurement errors owing to variations in the dye injection volume, the sampling volume, and timing the interval between samples.

The Fick method does not provide continuous monitoring and thus there is a possibility of that if a catastrophic event occurs, the response time to this event can be significantly lengthened. Finally, because this method demands frequent invasive injections, there is a continuing possibility that an infection will result from the dye solutions or the equipment.

A more commonly performed method for measuring cardiac output is the thermodilution technique. This method consists of injecting a known amount of cold saline through a catheter lumen into the right atrium of the heart to cool the blood in the vicinity of the catheter tip. By measuring the temperature of the blood distal to the injectate and taking into consideration the distance the cooled blood has flowed and the time interval between measurement and injection, the cardiac output can be determined.

Other thermal techniques use methods similar to the thermodilution system described above. Instead of a cool injectate, however, the blood is heated with a bolus of heated fluid. Then the temperature of the blood is measured and the determination of cardiac output is similarly computed. This thermal dilution technique typically requires local blood temperature increases on the order of 10° C. to obtain adequate correlations. A significant disadvantage associated with these high temperature increases is the potential damage to blood proteins and other tissue. Additionally, these thermal dilution methods require lengthy measurement periods which result in long delays between measurements.

More recent developed cardiac output monitors include those based upon a variation of the thermodilution systems. Such monitors depend upon an initial thermodilution measurement to provide an initial cardiac output determination and a constant associated with that method. The constant is thereafter utilized in combination with the results of blood velocity measurements to provide cardiac output information. During the velocity measurements, many of these systems utilize self-heating thermistors which allow only intermittent measurements and precludes continuous uninterrupted real-time velocity measurements.

An alternative method which relates to thermodilution techniques utilizes a long heating element mounted on a catheter proximally to a temperature sensor. The heating element is pulsed every 2–6 minutes with electrical power of 5–15 watts, causing the surrounding blood to rise in temperature. At the distal end of the catheter the temperature sensor measures the temperature of the heated flowing blood and the cardiac output is determined from a standard temperature dilution curve.

Though widely utilized, thermodilution techniques have a number of other disadvantages. More particularly, thermodilution procedures can be expensive because they require highly trained healthcare professionals and specialized equipment. Additionally, these techniques are incapable of real time continuous cardiac output determinations, but provide only intermittent output information. Moreover, active intervention is required in order to initiate the measurements, thus providing a certain level of risk. This risk is amplified by the risk of infection with each injection of cold saline. Furthermore, there tends to be a wide variation in measurements which necessarily requires three or more cardiac output readings so that the results can be compared. With respect to those systems which combine thermodilution techniques with blood velocity measurement techniques, these systems have the above-described disadvantages of thermodilution methods and require complicated equipment because thermodilution and velocity measurement capabilities are necessary.

A third method is known as the mixed venous oxygen saturation ($S_vO_2$) method and consists of measuring the oxygen level in the venous blood. Then, assuming that the rate of oxygen consumed is directly proportional to cardiac output, the blood flow rate can be determined. A serious problem which frequently causes inaccurate blood flow determinations when the venous oxygen saturation method is utilized is that many factors affect the measurement of oxygen. Besides cardiac output these factors include catheter placement, tissue perfusion, and HCT. Thus, this indirect method merely implies a cardiac output, and depending upon other factors, its accuracy can be questionable.

Other recent developments in the area of cardiac output monitoring include the incorporation of doppler probes on catheter tips to measure velocity and artery cross sectional areas from which cardiac output is calculated. These methods, however, are plagued with errors associated with catheter position and errors in the measurement of cross sectional areas.

Accordingly, there is a need to provide apparatus and methods for continuously and accurately providing real-time information relating to cardiac output, in the form of volume blood flow. There is also a need to provide apparatus and associated methods for monitoring cardiac output which results in a reduced likelihood of a catastrophic event occurring which goes undetected. Additionally, there is a need to provide a method for monitoring cardiac output in which the risk of infection is eliminated or significantly reduced.

SUMMARY OF THE INVENTION

The present invention provides apparatus and methods for the accurate and continuous determination of cardiac output in the form of blood volume flow. Because the apparatus of the present invention provides information on a continuous real-time basis and there is no significant lapse of time between measurements, there is a highly reduced likelihood that a catastrophic event will go unnoticed. Accordingly, the response time to medical intervention in the event of a significant event is reduced. Moreover, there is a significant reduction or elimination of risk of infection because the practice of the present invention does not include thermal dilution techniques which require the frequent injection of fluids to obtain cardiac output measurement.

The present invention provides apparatus for measuring fluid volume flow which includes a support member having a distal end, a proximal end, and an outer wall with a first temperature sensing means for sensing fluid temperature positioned on the support member outer wall. A second temperature sensing means is positioned apart from the first temperature sensing means and juxtaposed to a generally tubular heat transfer device which is radially disposed about the support member outer wall. As will become evident during the discussion below, the heat transfer device is a feature of the present invention which promotes efficient radial dissipation of heat without causing an increase in the temperature of the fluid medium. Importantly, the heat transfer device directly contributes to the ability of the monitor to directly determine fluid volume flow. More specifically, the heat transfer device is positioned apart from the first temperature sensing means, juxtaposed a second temperature sensing means and includes an electrically insulated heating means positioned between a temperature equilibrator, such as, for example, a heat conducting material, and an insulating material. The temperature equilibrator or heat conducting material is in contact with the second temperature sensing means and provides a means to integrate or normalize the temperature surrounding the second heat sensing means.

In order to provide information relating to the temperatures at the first and second temperature monitoring means, at least one temperature monitoring means is placed in communication with the first and second temperature sensing means. Similarly, in order to supply and control power to the heating means a power supply and current control means are placed in communication with the electrically insulated heating means. Preferably, the power supply, current control means, and temperature monitoring means are interactively controlled bye central microprocessor which further provides visual information during monitoring procedures.

In preferred embodiments, the support member utilized in the apparatus of the present invention is a catheter dimensioned for placement within a patient's body cavity having blood flow. Preferred catheter support members further include an inflatable device positioned on the outside wall distal to the heat transfer device and the first and second temperature sensing means. Also in accordance with the present invention, the first and second temperature sensing means are preferably each thermistors; the electrically insulated heating means is preferably a high resistance nickel alloy filament in the form of a coil; the temperature equilibrator is a gold plated copper bushing, and the insulating material is biocompatible polymer.

The apparatus of the present invention can be utilized to determine cardiac output by positioning the catheter support member at a predetermined location within a body cavity having flowing blood, a blood flow direction, and a blood temperature. Next, monitoring the first temperature sensing means provides a determination of blood temperature, and providing power to the electrically insulated heating means provides a second temperature sensing means temperature, the difference between the blood temperature and the second temperature sensing means temperature providing a temperature differential. The next steps includes monitoring the second temperature sensing means temperature while allowing heat to dissipate radially from the electrically insulated heating means through the biocompatible material and the temperature equilibrator or heat conducting material, and simultaneously providing power to the electrically insulated heating means to maintain the temperature differential. Heat dissipates at a rate which is proportional to the blood volume flow. Thus, the power required to maintain the temperature differential is proportional to blood volume flow. Accordingly, by determining the power required to maintain the temperature differential, the blood volume flow is known.

Advantageously, the apparatus of the present invention provide accurate and continuous real-time information relating to cardiac output and blood temperature without subjecting the patient to exposure to dyes or unnecessarily high temperatures. Additionally, the present invention can be practiced without the need for high cost equipment and the constant attention by highly trained personnel.

Generally, the catheter support members utilized for monitoring fluid flow in accordance with the present invention can be formed according to well known methods within the art. These methods include extruding the support means and mounting the first and second temperature sensing means and the heating means on the outer walls using conventional techniques such as adhesives and heat bonding. Preferred heat transfer devices are fabricated by forming an appropriately sized high resistance wire coil over gold plated copper bushing and depositing a layer of insulating material using plasma deposition techniques. Finally, suitable power supplies, power controllers, and monitors are commercially available for use in the present invention.

Further objects and advantages of the apparatus for monitoring fluid volume flow of the present invention, as well as a better understanding thereof, will be afforded to those skilled in the art from a consideration of the following detailed explanation of preferred exemplary embodiments and the drawings.

A BRIEF DESCRIPTION OF THE DRAWINGS

FIG. 1 is a schematic representation of an apparatus for monitoring fluid volume flow in accordance with the present invention.

FIG. 2 is a perspective schematic illustration and cut away view of a heat transfer device and second temperature sensing means in accordance with the present invention.

FIG. 3 is an end cross-sectional view of the heat transfer device and second temperature sensing means of FIG. 2.

FIG. 4 is an enlarged longitudinal cross-sectional view taken from the portion indicated as area AA of the heat transfer device of FIG. 5.

FIG. 5 is a longitudinal side view of the heat transfer device of FIGS. 2–4 fitted on a portion of a support member.

FIG. 6 is a longitudinal cross-sectional view of an alternative embodiment heat transfer device of the present invention shown on a section of a support member.

FIG. 7 is an enlarged view taken from area A of the heat transfer device of FIG. 6.

FIG. 10 is a "split-heating coil" configuration of heat transfer device of the present invention and corresponds to the heat transfer device of FIG. 5.

FIG. 11 is a "split-heating coil" configuration of a heat transfer device of the present invention and corresponds to the heat transfer device of FIG. 8 and further indicates a second insulating layer.

FIG. 12 is a "split-heating coil" configuration of a heat transfer device of the present invention and corresponds to the heat transfer device of FIG. 8.

FIG. 15 illustrates a general cardiac output monitor utilized in the explanatory examples herein and shows the details of a general longitudinal side view of a catheter body, thermistors and heat transfer device utilized to obtain data.

FIG. 16 is cross-sectional view illustrating the configuration of each lumen of the catheter body of FIG. 15.

FIG. 17 is a side longitudinal view of the heat transfer device of FIG. 15 and shows a cut away view of second thermistor.

Figure 19:
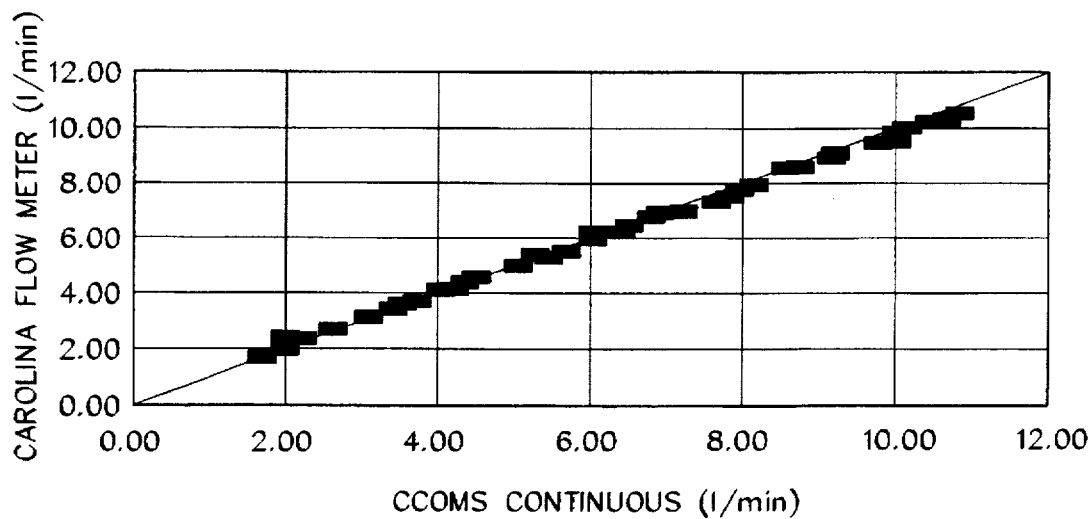

FIG. 19 graphically shows the results of in vitro data obtained in the right heart circulation system utilizing an exemplary cardiac output monitor of the present invention compared with an electromagnetic volume flow detector.

Figure 20:
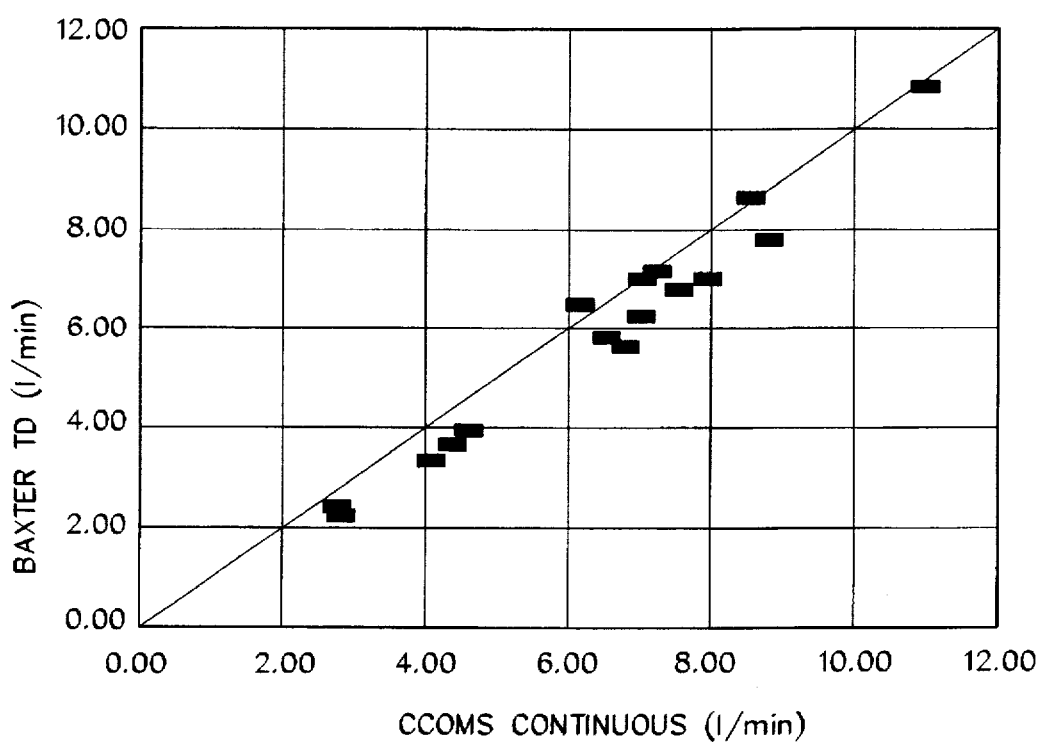

FIG. 20 compares the results of in vivo data obtained using a cardiac output monitor of the present invention and a prior art thermal dilution monitoring apparatus.

DETAILED DESCRIPTION OF EXEMPLARY EMBODIMENTS

The teachings of the present invention provide apparatus which can be miniaturized and inserted in small areas. Accordingly, the practice of the present invention is particularly suitable for applications in which small volumes of fluid flow are measured. However, those skilled in the art will appreciate that the present invention can be practiced in any situation requiring the direct measurement of fluid volume flow, and thus is not limited to a specific application. For purposes of explanation only, the apparatus and methods described herein are considered in the context of monitoring cardiac output wherein blood volume flow is determined directly and continuously using the monitoring apparatus described below.

Turning now to FIG. 1 there is shown a schematic representation of an exemplary apparatus 10 for measuring cardiac output in accordance with the present invention. The apparatus 10 includes a support member 12 having a distal end 14, a proximal end 16, and an outer wall 18. A first temperature sensing means 20 for sensing fluid temperature, is positioned on the support member outer wall 18. In a most preferred embodiment of the present invention, a heat conducting material layer 19 having a thickness of from 0.002 inches to about 0.006 inches is radially disposed about first temperature sensing means 20 and serves to dissipate any heat generated by the first temperature sensing means 20. A second temperature sensing means 22 is positioned apart from the first temperature sensing means 20 and juxtaposed to a generally tubular heat transfer device 24 which is radially disposed about the outer wall 18. As discussed with further detail below, first and second temperature sensing means are in communication with temperature monitoring apparatus. For ease of illustration the temperature monitoring apparatus is not shown in the general illustration of FIG. 1.

FIG. 2 is a perspective view of a portion of apparatus 10 and illustrates an exemplary heat transfer device 24 in accordance with the present invention. More particularly, generally tubular heat transfer device 24 of FIG. 2 includes an electrically insulated heating means 26, in communication with a power supply and power controlling means (not shown in FIG. 2), and sandwiched between a temperature equilibrator or heat conducting material 28 and an insulating material 30. Cross-sectional views of heat transfer device 24 are presented in FIG. 3, an end cross-sectional view, and FIG. 4, an enlarged longitudinal cross-sectional view taken from view 4—4 of FIG. 5, wherein electrically insulated heating filament 26, heat conducting metal bushing 28, and insulating material 30 are shown as concentric layers and form the tubular configuration of heat transfer device 24. Moreover, the layers are configured so that the layer of heat conducting metal 28 is in contact with second temperature sensing means 22 and electrically insulated heating means 26. FIG. 5 further illustrates heat transfer device 24 fitted on a portion of a support member 11 which comprises tubing in the present embodiment. Also shown in FIG. 5 is a preferred positioning of second temperature sensing means 22 which is shown embedded in outer wall 18. Referring again to FIG. 2 and FIG. 5, in the preferred embodiment insulating material 30 is positioned to be in contact with fluid during apparatus use.

An alternative heat transfer device configuration is illustrated in FIG. 6 and FIG. 7, wherein the heat transfer device and temperature sensing means are indicated at numerals 31 and 32, respectively. More particularly, FIG. 6 is a longitudinal cross-sectional view of heat transfer device 31 shown on a section of a support member 33 (body tubing), and FIG. 7 is an enlarged view taken from area A of FIG. 6. Heat transfer device 31 includes heating means 35 in the form of a high resistance filament coil radially disposed about a heat conducting material layer 39 and temperature sensing means 32 in the form of a filament coil in contact with heating means 35, also radially disposed about heat conducting material layer 39. Temperature sensing means coil 32 and heating means coil 35 are adjacent an insulating material layer 41 with insulating material layer 41 further bordered with a biocompatible material layer 45. Suitable heat conducting material layers 39 include stainless steel bushings which are radially disposed about support member 33 and suitable heating means coil include those fabricated of high resistance nickel alloy filament. Temperature sensing means coil 32 can be, for example, platinum wire or any material having an electrical resistance which measurably changes with small changes in temperature. Insulating material layer 41 can be any non-conducting material including a variety of organic polymers. Suitable biocompatible material layers include biologically inert metal plated materials such as gold or silver plated copper bushings. As mentioned above, and illustrated in FIG. 6, second heat conducting material layer 45 and first heat conducting material layer 53 extend beyond heating means coil 49.

Figure 9:
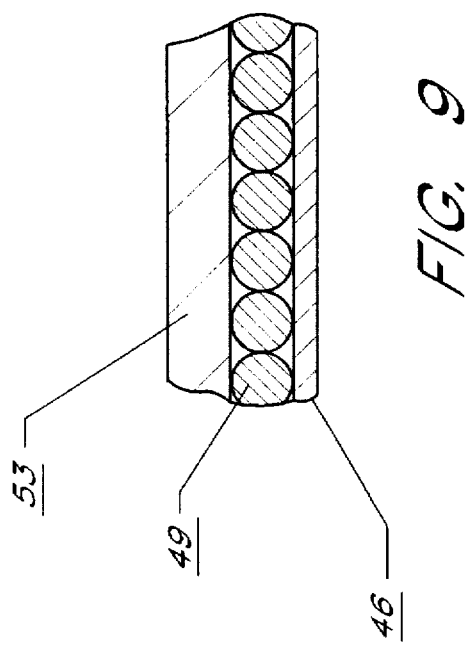
FIG. 9 is an enlarged view of area B of the heat transfer device of FIG. 8.
Figure 8:
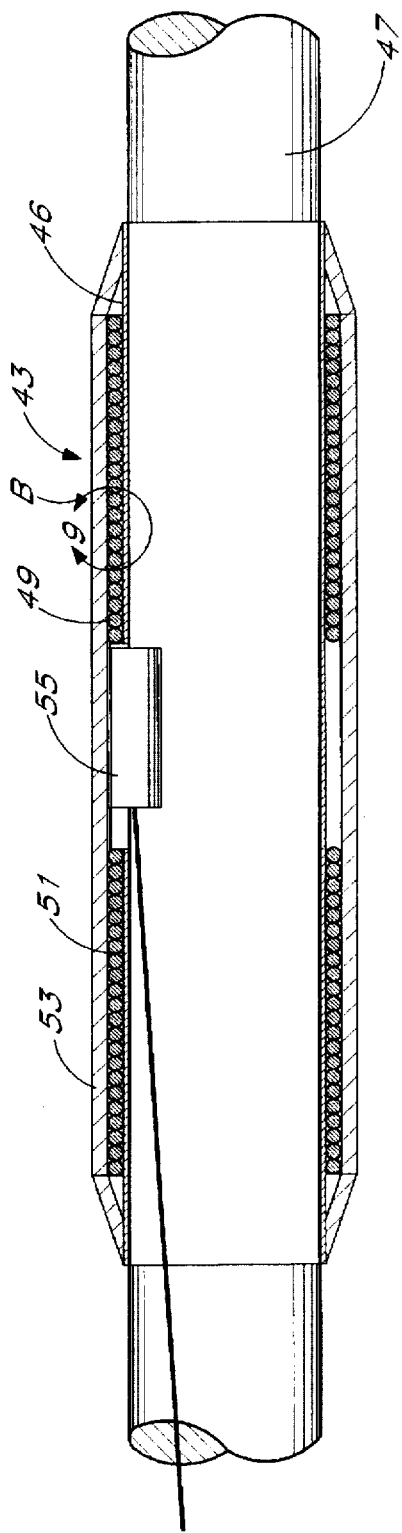
FIG. 8 is a longitudinal cross-sectional schematic illustration of an alternative embodiment heat transfer device of the present invention.

Another alternative heat transfer device 43 is illustrated in the longitudinal cross-sectional view of FIG. 8 and the enlarged view of FIG. 9 taken from area B of FIG. 8. Heat transfer device 43 includes a first heat conducting material layer 46 radially positioned about support member 47 and bound by a heating means 49 in the form of a coiled heating filament. An insulating material layer 51 is in contact with heating means coil 49 which in turn is adjacent a second heat conducting biocompatible material layer 53. In this embodiment, second temperature sensing means 55 is embedded in the wall of support member 47 and in contact with second heat conducting biocompatible material layer 53 and first heat conducting material layer 46 which serve as temperature equilibrators as explained in more detail below. As mentioned above, and illustrated in FIG. 8 second heat conducting material layer 53 and first heat conducting material layer 46 are longer in length than and extend beyond heating means coil 49.

As a feature of the present invention, the various embodiments of the heat transfer device are advantageously configured and materially designed to dissipate heat radially from a heating means in a highly efficient manner. The following discussion is made in reference to the preferred heat transfer device of FIGS. 2–5, however, the described materials and their functions apply equally to the alternative embodiments of FIGS. 6–9. More particularly, the choice of materials for each of the elements of heat transfer device 24 is dependent upon the range of fluid volume flow, the heat capacity of the fluid, the fluid temperature as well as the temperature differential described below. Heat transfer device 24 preferably includes heating means 26 in the form of a cylindrical coil fabricated of high resistance nickel alloy filament with each turn of the coil in contact with adjacent turns. The dimensions of the high resistance nickel alloy filament can vary, however typically the filament is from about 2 feet to about 6 feet in length and has a diameter of from about 0.002 inches to about 0.005 inches. Additionally, the coil has an overall length of from about 0.2 inches to about 0.5 inches.

As further illustrated in FIG. 2 heat conducting metal layer 28 is coextensive with insulating material layer 30 and electrically insulated heating filament 26 has a shorter overall length than heat conducting metal layer 28 and insulating layer 30. For preferred heat transfer devices, heat conducting layer is gold plated copper bushing having a length of from about 0.3 inches to about 0.6 inches, an internal diameter of from about 0.07 inches to about 0.095 inches, and a wall thickness of from about 0.002 inches to about 0.006 inches. With respect to insulating material layer 30, this is preferably thermally conductive, non moisture absorbing, biocompatible and most preferably a blood compatible material such as a hydrophobic biocompatible polymeric material. Most preferably layer 30 is a polyxylylene which is commercially available from Paratech under the tradename PARYLENE C. Appropriately, PARYLENE C is inert, bonds well to a variety of surfaces, transfers heat, and does not absorb moisture. The thickness of the layer of polyxylylene must be thick enough to electrically insulate and thin enough to dissipate small amounts of heat. It has been found that suitable polyxylylene layers or coatings can be formed by depositing polyxylylene using plasma deposition techniques known in the art to provide a layer thickness of from about 0.0002 inches to about 0.0007 inches.

Further and in accordance with the present invention, the above-described heat transfer devices can be configured with a "split-heating coil" design. More particularly, and referring to FIGS. 10–12 there are shown "split-heating coiling" configurations of which FIG. 10 generally corresponds with FIG. 5 and FIGS. 11–12 generally correspond to heat transfer device of FIG. 8 and wherein like numerals correspond to their corresponding FIGS. As can be seen, the "split-heating coil" heat transfer devices of FIGS. 10–12 have a general tubular configuration with the heating coil split on either side of a second heat sensing means. These configuration physically isolate heating coil from heat sensing means while retaining the equilabrator features of the heat conducting materials which are in contact with second heat sensing means.

In accordance with the present invention preferred fluid volume flow monitors incorporate second temperature sensing means which are positioned in a slot in support body. This particular configuration is illustrated most pronouncedly in FIG. 8 and is also the configuration of the heat transfer device of FIG. 5. Additionally in accordance with the present invention a second heat insulating layer, shown as numeral 23 in FIG. 2 and FIG. 11 is disposed adjacent second temperature sensing means 22, 55 opposite the temperature equilibrator or heat conducting layer 28, 53. Latex sheet available from McMaster Carr of Santa Fe Springs, Calif. has been found to be suitable for fabricating heat insulating layer 23. The combination of heat insulating layer 23 and heat conducting layer 28, 53 in contact with second temperature sensing means 22, 55 allows for reading of an equilibrium, normalized or integrated temperature that is directly related to the amount of fluid volume flow in the medium surrounding the heat transfer device. As an additional feature, the presence of the heat conducting layer in contact with second temperature sensing means 22 facilitates the dissipation of heat generated by any self heating of the second temperature sensing means 22 and continuously provides an indication of increase or decrease in heat dissipated by the heat transfer device. As will be explained in greater detail below, an increase in power to electrically insulated heating means is provided in response to a decrease in the temperature at temperature sensing means 22. The decrease in temperature in turn is attributed to an increase in heat dissipation caused by an increase in fluid volume flow.

In accordance with the present invention, the first and second temperature sensing means 20, 22 can be a thermistor, a thermocouple, or any means known in the art for detecting temperature or temperature changes. The actual choice of temperature sensing means is dependent upon design configurations and particularly the range of temperature and temperature differentials which are under consideration. Preferably, temperature sensing means 20, 22 are thermistors of the type which detect small changes in temperature, on the order of less than 0.05° C. with precision and reliability. Suitable thermistors are available from Thermometrics Corporation located in Edison, N.J. Those skilled in the art will appreciate that combinations of different types of temperature sensing means can be utilized as first and second temperature sensing means.

For purposes of measuring cardiac output the support member 12 is preferably a catheter body dimensioned for placement within a patient body cavity having flowing blood. Such cavities include, but are not limited to, the pulmonary artery, the right ventricle, right atrium, vena cava, aorta, and other major arteries. Advantageously, suitable catheter support members can be any of numerous catheters which are commercially available and which provide various additional functions. More particularly, suitable catheter support members simultaneously can provide additional functional features and remain easily inserted into a patient body. For example, catheters known in the art for providing pulmonary artery pressure (PAP), wedge pressure (PAOP), and central venous pressure (CVP) or $SVO_2$ can incorporate the thermistor and heat transfer device of the present invention without interfering with catheter function and insertion. These catheters are normally fabricated from biologically compatible materials such as plasticized polyvinylchloride, polyurethanes, polyethylenes, polypropylenes, or nylons which are easily formed into elongated flexible tubular configurations.

Figure 13:
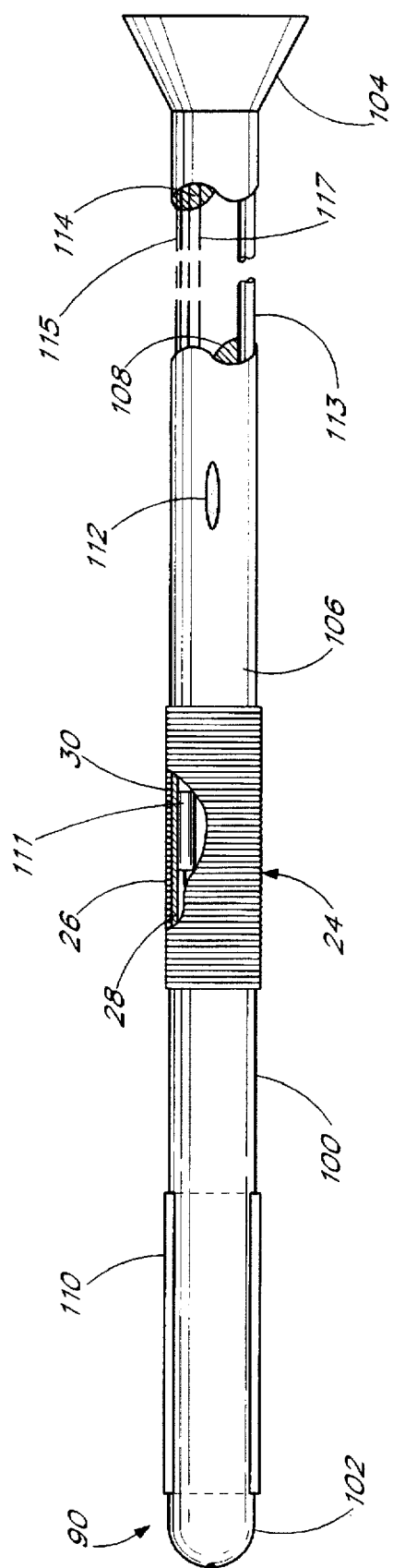
FIG. 13 illustrates a cardiac output monitor apparatus of the present invention.

It should be noted at this point that the general configuration of fluid volume flow monitor of FIG. 1 and the cardiac output monitor described below and generally shown in FIG. 13 is designed for measuring fluid or blood having a flow direction from the proximal end to the distal end of the support member. In preferred cardiac output applications wherein support member 12 is positioned in a pulmonary artery, the relative location of first temperature sensing means 20 and heat transfer device 24 is as shown with heat transfer device positioned distal to first temperature sensing means. However, those skilled in the art will recognize that when measuring fluid or blood having a flow direction from distal end to proximal end, the relative positions of first temperature sensing means 20 and heat transfer device 24 are reversed. This application is used, for example, when measuring blood flow in the left circulation such as within the aorta and other major arteries.

FIG. 13 illustrates a cardiac output monitor apparatus 90 of the present invention which includes a catheter body support member 100 having a distal end 102, a proximal end 104, a catheter body wall 106, and at least one lumen 108 integral therewith. An inflatable device 110 is positioned on catheter body wall 106 distal to heat transfer device 24 which is substantially the same heat transfer device 24 of FIG. 2–FIG. 4. First thermistor 112 for sensing blood temperature is positioned on an outer surface of catheter body wall 106 and away from heat transfer device 24. A second thermistor 111 is embedded in catheter body wall 106 and juxtaposed to heat transfer device 24. Catheter body support member 100 preferably also includes a means for inflating (not shown) the inflatable device in fluid communication with the inflatable device through the at least one catheter lumen 108. Preferably, inflatable device 110 is a balloon, as shown, however, a number of different devices can be utilized including blisters. As described below, when inflatable device 110 is inflated and in use, it allows for the proper floatation of the catheter into the desired position for measuring blood volume flow.

Inflation line 112 is utilized functionally as a conduit for the application of fluid, including air, to inflatable device 110. Electrical wire bundles 114, 115, 117 enter catheter body 100 at proximal end 104 and extend through lumen 108 to thermistors 112, 111 and heating filament 26, respectively. More particularly, and as discussed below, wire bundles 114, 115, and 117 include live and return connections and extend between a microprocessing unit and first and second thermistors 111, 112 and heating filament 26 respectively.

Those skilled in the art will recognize that catheter body support member 100 can have one lumen in communication with first and second thermistors 112, 111, heating means 26, and balloon 110. However, those skilled in the art, however, will recognize that catheter body support member 100 also can have a plurality of lumens, each lumen communicating with one of the first and second thermistor, heating means, or balloon. For example, one lumen can communicate with first thermistor 112 and contain live and return wires for the first thermistor connecting the temperature monitor means. Similarly, a second lumen can communicate with the second thermistor 111 and contain live and return wires for the second thermistor connecting with the temperature monitoring means. A third lumen can communicate with the electrical resistance heating coil 26 and thereby connecting the power supply with the electrical resistance filament.

Figure 14:
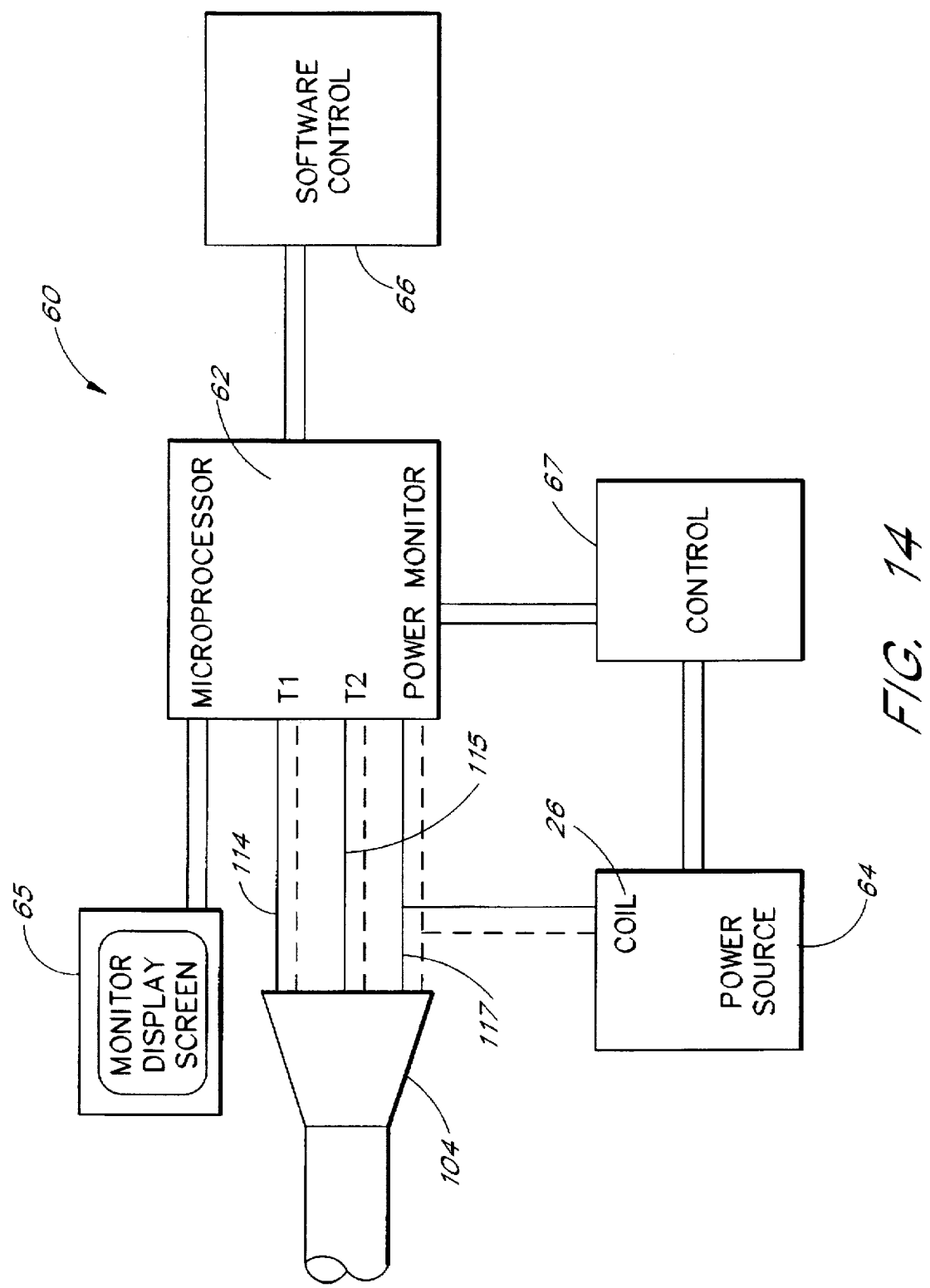
FIG. 14 is a diagrammatic illustration of a system for monitoring cardiac output in conjunction with the use of cardiac output monitor apparatus shown in FIG. 13.

As already mentioned, in order to monitor, control, and provide cardiac output information to a user, the present invention additionally contemplates a system which further includes instrumentation for controlling and supplying power, performing monitoring, controlling, and information display functions. Referring to FIG. 14 there is shown a diagrammatic illustration of a system 60 for monitoring cardiac output in conjunction with the use of cardiac output monitor apparatus 90 as shown in FIG. 13. For ease of illustration, only proximal end 104 of catheter body 100 and wire bundles 114, 115, and 117 which include live and return connections to first and second thermistors and heating filament are identified in FIG. 14. More particularly, system 60 includes microprocessor unit 62 in electrical communication with power supply 64, first thermistor 112, second thermistor 111, high resistance heat filament coil 26 and user monitor display 65. As explained in more detail below, microprocessor unit 62 is a conduit for temperature information to and from first and second thermistors 112, 111 and for information to and from power supply 64 through power supply control and temperature control unit 67. As such, microprocessor unit 62 includes first and second temperature monitors 68 and 69. Further, microprocessor unit 62 receives calculated information relating to volume flow parameters from software control unit 66 and in turn sends power information to software control 66 which is additionally in communication with monitor display 65.

It is also contemplated to be within the scope of the present invention to provide visual and or audible display devices or signal monitoring devices which can be activated by the temperature monitoring means and the electrical current control means. It is also preferred that the temperature monitoring means, the electrical current controlling means and the display device are integral with a microprocessor control system which is appropriately designed to provide continual and instantaneous indications of cardiac output and or blood ambient temperature to the professional user.

In accordance with the present invention a generalized process for monitoring cardiac output is provided which includes first providing a cardiac output monitor system which includes the cardiac output monitor apparatus 90 of FIG. 13 and instrumentation for controlling and monitoring apparatus functions as shown generally in diagrammatic system 60 of FIG. 14. Continuously determining blood volume flow is accomplished by first positioning catheter body support member 100 at a predetermined location within a body cavity having a flowing blood direction, and a blood temperature. The next step involves utilizing temperature monitoring means 68 to monitor first thermistor 112 and determine blood temperature. Then by providing power to electrically insulated heating filament 26 from power source 64 as controlled by unit 67 a heating filament temperature is created, thereby generating a temperature differential between the blood temperature and the heat transfer device equilibrium temperature. The process further includes monitoring second thermistor 111 by monitor 69 and simultaneously allowing heat to dissipate radially from the electrically insulated heating filament 26 through biocompatible material layer 30 and heat conducting metal layer 28. Finally, by controlling power to the electrically insulated heating filament 26 in order to maintain the temperature differential between blood temperature and the equilibrium temperature of the heat conducting layer 28, and monitoring the amount of power required to maintain the temperature differential, blood volume flow is continuously determined, the power required to maintain the temperature differential being proportional to blood volume flow. Stated differently, the rate of heat dissipation through heat conducting metal layer 28 and biocompatible material layer 30 has been found to be proportional to the blood volume flow.

Once a catheter body support member is placed within a predetermined body cavity having flowing blood, the continuous determination of blood volume flow involves the interaction of the first and second thermistor, the power supply and the insulated heating filament as monitored and controlled by the microprocessor. Simultaneously, software keeps tracks of the predetermined temperature differential, and utilizes the power required to maintain the temperature differential as determined by the microprocessor to calculate blood volume flow and display the results to a user.

More particularly, the first thermistor provides a signal to the microprocessor to indicate blood temperature and the microprocessor causes the power supply to activate the high resistance heating filament to provide the high resistance heating filament with a predetermined temperature which is preferably about 0.3° C. to about 3° C. above blood temperature. The difference between blood temperature and predetermined equilibrium temperature of heat conducting layer 28 is termed the temperature differential. Meanwhile, in response to blood flow, the heat conducting metal layer and insulating biocompatible material layer of the heat transfer device efficiently and radially dissipate heat from the heating filament without causing a significant increase in blood temperature. This is because one watt of power equals 0.2387 cal/sec heat transfer. Since the maximum power at very high cardiac output is only 1 watt, the maximum heat transfer is only 0.2387 cal/sec.

The blood volume flow is determined continuously, because the microprocessor continuously monitors the first and second thermistor temperature and controls the power delivered from the power supply to the high resistance heating filament in order to maintain the predetermined temperature differential. In fact, first and second temperature sensing means and power required to maintain the temperature differential are monitored and adjusted at a rate of 15 times per second. Simultaneously, the microprocessor feeds power requirement information to software which uses the information to calculate blood volume flow. Preferably, the calculated blood volume flow and other relevant information is fed to a display monitor for observation by the user.

Additionally, data storage devices can be used to store the temperature, power, and calculated information.

It has been determined that in fact the rate of heat dissipation is dependent upon the actual blood volume flow and not simply the velocity of blood flow as can be seen from the general heat transfer formula:

$$q = mC_p(T_s - T_b)$$

where:

$q$=rate of heat transfer=power (Watt)×0.2387 cal/sec. Watt×60 sec/min $m$=mass flow=volume flow (cc/min)×fluid density (1.056 g/cc)

$C_p$=specific heat of fluid (0.087 cal/g-sec)

$T_s$=Temperature of heating means or heat conducting metal $T_b$=Temperature of blood Thus, by determining the amount of current which is required to maintain a constant temperature differential a direct reading of changes in blood volume flow which is accurate and continuous can be determined. Depending upon a particular $T_s - T_b$, typically between about 0.3° C. and 3° C., the flow vs power relationship is illustrated in FIG.

Those skilled in the art will appreciate that the power supply can be monitored with relative ease in all of its aspects. Thus for example instead of current, other electrical indicators such as resistance and voltage can also be monitored to give the same accurate and continuous cardiac output determinations. In addition to monitoring the amperage supplied to the heating filament, and calibrating the monitored amperage to convert the readings into blood flow rate, voltage or resistance can also be measured. In all cases, compared to existing technologies, an exceedingly more accurate blood flow rate determination is provided with the added considerable advantage that the signal can be instantaneously monitored at any time interval or it can be continuously monitored.

As mentioned above, by providing microprocessor control of the process of the present invention very small changes in temperature between the first and second temperature sensing means will immediately signal the electric current control means to change the rate of current flow to the heating means in order to maintain the desired temperature differential of from about 0.3° C. to about 3° C. The microprocessor can then immediately translate this required decrease or increase in current to a quantitative expression of blood volume flow from a previously determined calibration. The microprocessor then provides an output signal for visually or audibly indicating accurate cardiac output in terms of blood volume flow. In fact, the microprocessor will process about 8 readings per second, therefore precluding any delay in calculating and displaying flow information.

The more accurate and continuous cardiac output monitoring provided by the process and apparatus of the present invention advantageously provides instantaneous indication of cardiac function, both trending and absolute. Because any response to catastrophic events which may occur can be more accurately and timely detected, the use of the apparatus of the present invention additionally increases the effectiveness of any medical intervention which may be required. Moreover, the likelihood of infection is substantially reduced because the process of the present invention does not require injectates such as cold and hot solutions or dyes.

The just described apparatus and process for monitoring cardiac output can be incorporated within a catheter or other supporting medium which is designed to provide medical indications in addition to cardiac output. For example, a 6 lumen Swanz-Ganz type catheter can be designed to incorporate the features of the present invention as well as perform certain pressure monitoring functions for which this type of catheter is known. Thus, the central lumen of a Swanz-Ganz catheter can incorporate a transducer for monitoring pulmonary artery pressure. Since the preferred blood vessel location for positioning the catheter for cardiac output monitoring is the pulmonary artery, the pulmonary artery pressure monitor provides an indication as to whether the distal end of the catheter is in the ventricle or the artery. Accordingly, in addition to providing continual pressure monitoring, this information allows the medical professional to effectively position the catheter within the pulmonary artery for monitoring cardiac output.

Another catheter lumen of the six lumens of a Swanz-Ganz type catheter can provide the communication for an injectate for central venous pressure monitoring in the same manner as currently provided. The remaining four lumens can each separately provide the access for the fluid and electrical communications described above for the cardiac output monitor of the present invention. Accordingly, two of the four lumens contain the live and return wires for the first and second temperature sensing means. These wires are accessed through the electrical wire port as described above. A third lumen similarly contains the wires for communication between the power supply and the heating means and the fourth provides the route for inflating the inflation device and is accessed from the means for inflating through the inflation port.

The apparatus of the present invention can be fabricated using common assembling techniques available to those skilled in the art of designing and forming catheters for medical use. For example, single and multi-lumen catheters are both readily available commercially and they can be formed using common polymeric extrusion techniques known in the industry. Thermistors are conveniently and advantageously mounted on the outer wall of the catheter using well known methods such as adhesive bonding. Suitable heat transfer device are prepared by forming a healing coil from a suitable high resistance filament over a sheath or bushing of heat conducting metal. As mentioned above, preferably the heat conducting metal sheath or bushing is longer in length than the coil, and the coil is longitudinally centered over the bushing. The insulated material layer can then be formed over the exposed heat means coil and sheath or bushing by means known in the art including the preferred method of plasma vapor depositing a layer of PARALYNE. Finally the assembled heat transfer device is conveniently slipped over the catheter body support member and secured to the body juxtaposed to the second heat sensing means.

The following non-limiting examples refer to a preferred cardiac output monitor apparatus as generally shown in FIGS. 15–17. The data illustrate the accuracy and the continuous performance of cardiac output monitors described herein and further confirm that in fact blood volume data is proportional to and indicated by the rate of heat dissipation through the heat transfer device.

EXAMPLE 1

A number of six lumen catheters fabricated of polyvinylchloride according to methods known in the art were prepared. A general longitudinal side view of these catheters is shown in FIG. 15 and a cross-sectional view illustrating the configuration of each lumen in shown in FIG. 16. The catheters have a body 200 a distal end 202, a proximal end 204 and an inflatable balloon 206. The six lumens functioned as follows: 208 was a proximal injectate lumen for injecting fluids or medicines as need; 210 was a proximal thermistor lumen for communicating wire bundles from microprocessor, temperature monitor and first thermistor 212; 14 was a distal thermistor lumen for communicating wire bundles between microprocessor, temperature monitor and second thermistor 216 shown in the heat transfer device 218 of FIG. 17 (taken at C of FIG. 15); 220 was a thermal coil lumen for communicating wires between the microprocessor, power supply and high resistance heating coil 222; 224 was a pulmonary artery distal infusion lumen; and 226 was a balloon inflation lumen for communication air to balloon 206.

Each catheter was fitted with first and second thermistors 212, 216 purchased from Thermometrics. The particular heat transfer device of FIG. 2–FIG. 4 (shown without full detail as two the concentrically form layers at FIG. 17) was prepared by forming a cell of nickel copper filament around a Gold plated copper bushing and then forming a layer 223 of PARYLENE C by plasma depositing the polymer on to the nickel alloy filament. The particular dimensions of each component of the heat transfer device were as follows. The gold plated copper bushing had a bushing length of 0.51 inches, a bushing internal diameter of 0.085 inches, and 0.003 inch wall thickness. The nickel copper coil was prepared from a 30 inch length of nickel copper 110 ohm filament having a diameter of 0.003 inches. A layer of PARYLENE was vapor deposited to a layer thickness of 0.0005 inches about the exposed bushing and exposed portions of the heating coil. The completed heat transfer device was then fitted into position radially about the second thermistor embedded in the wall of the catheter body. Each of the thermistors and the heating means were connected to their respective monitors and controllers as generally shown in system 60 of FIG. 14.

Figure 18:
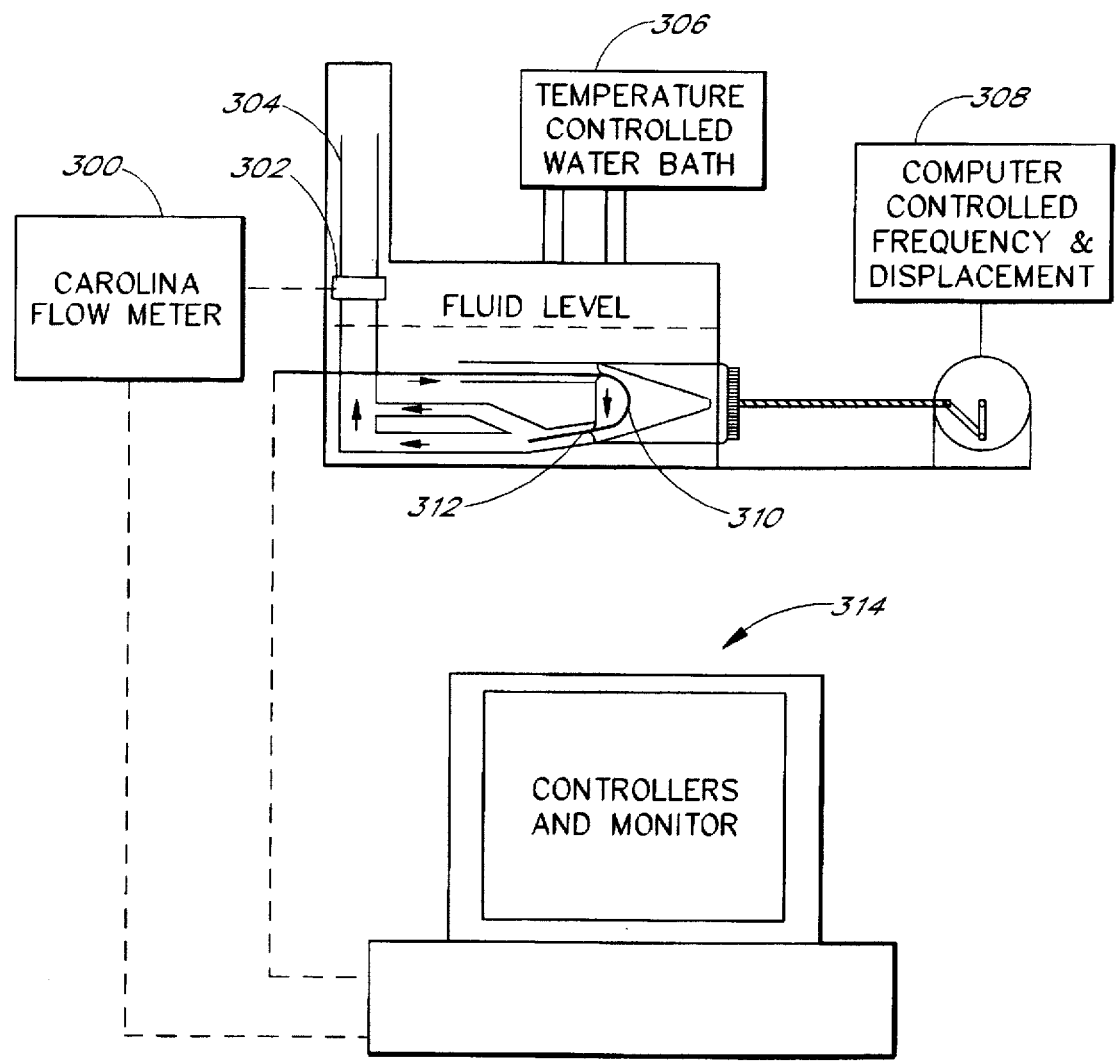
FIG. 18 is a diagrammatic view of a right heart circulation system utilized to obtain in vitro fluid volume flow data according to the process of the present invention.

The above-described cardiac output monitoring system was then used to obtain in vitro fluid volume flow data in the lab using a right heart circulation system illustrated in FIG. 18 having a Carolina Flow Meter 300, a flow probe 302, a water column 304, a temperature controlled water bath 306, a computer controlled frequency and displacement device 308, a cardiac output monitor apparatus 310, a tri-leaflet valve 312, and controllers and monitor 314. In use in the system of FIG. 18, the above-described cardiac output monitor was floated into a position designed to simulate placement in the pulmonary artery. In addition to obtaining data using the cardiac output monitor of the present invention, electromagnetic flow meters purchased from Carolina Medical were used to obtain comparison data. The results of the in vitro comparison data obtained in the right heart circulation system are shown graphically FIG. 19. As shown in FIG. 19, there was excellent correlation between continuous cardiac output readings obtained utilizing the cardiac output monitor of the present invention and those obtained with the electromagnetic flow meter, a well known highly accurate and precise method for determining volume flow but not adaptable to physiological conditions. In fact there is nearly overlying reproducibility of data obtained using the apparatus of the present invention with the electromagnetic flow meter.

EXAMPLE 2

Five of the cardiac output monitors prepared as described above in Example 1 were utilized to obtain in vivo cardiac output data in five healthy sheep. Each of the five cardiac output monitors was floated into position within the pulmonary artery of each of the sheep and blood flow information was obtained continuously and in real time. Comparison data was obtained using a thermal dilution method provided by Baxter Healthcare's COM-2 cardiac output monitor, a well known clinically utilized intermittent, noncontinuoue cardiac output monitor. As shown in FIG. 20, there was excellent correlation between the continuous real time cardiac output data obtained with the apparatus of the present invention and data obtained using the less desirable conventional intermittent thermodilution technique.

Clearly, the above examples illustrate the ability of the cardiac output monitoring apparatus of the present invention to provide accurate volume flow information without thermal dilution steps.

It is further contemplated as being within the scope of the present invention to provide a cardiac monitoring apparatus which includes a catheter body support member having one thermistor and one heat transfer device. The thermistor is juxtaposed to the heat transfer device and provides an indication of blood temperature intermittently. Simultaneously with determining blood temperature, a power supply provides power to a heating filament to generate a temperature differential between the just determined blood temperature and the heating filament. The one thermistor provides an indication of heating filament temperature to the microprocessor and/or temperature monitoring means. This information is used to provide less or more power to the heating filament to maintain the temperature differential. The amount of power required to maintain the differential is used to determine blood volume flow. The thermistor can then provide an indication of blood temperature and the cycle starts again.

It is readily recognized by one skilled in the art that such a cardiac output monitor differs from the embodiments described above in that a second heat sensing means is not included. This apparatus can contain all other aspects described above including an inflatable device, electrical and inflation ports, and the accompanying instrumentation for monitoring and controlling the operating of the apparatus. Additionally, typical heating means, temperature sensing means and catheter materials as described above are applicable.

In operation, the process according to the present invention for utilizing this exemplary embodiment includes measuring an ambient blood temperature at the temperature sensing means. After the measurement, the heating means is activated to create a temperature differential between the just sensed ambient blood temperature and the heating means temperature. The energy required to achieve this temperature differential is measured by the associated controlling instrumentation. This energy is proportional to the blood flow rate and is an indication of the blood flow rate. Following this measurement, the heating means is deactivated and the heating means temperature return to ambient blood temperature. The ambient blood temperature is again monitored and the cycle is repeated. In this manner, cardiac output determinations can be made on a semi-continuous basis.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is limited only by the following claims.

What is claimed is:

1. An apparatus for placement within a body lumen having flowing fluid, said apparatus comprising:
   a support member having a distal end, a proximal end, and an outer wall;
   a temperature monitor;
   a first temperature sensor configured to sense a first temperature of the fluid within said body lumen, said first temperature sensor positioned along an outer surface of said outer wall and in communication with said temperature monitor;
   a second temperature sensor positioned along said support member and in communication with said temperature monitor;
   a heat transfer device radially disposed about substantially the entire periphery of a segment of said outer wall, said heat transfer device further disposed apart from said first temperature sensor and juxtaposed said second temperature sensor, said heat transfer device comprising:
      a power source;
      an electrically insulated heating device in communication with said power source and positioned between a heat conducting layer and an insulating layer, said insulating layer forming an outer layer of said heating device such that said insulating layer is in contact with said fluid and said heating device is in thermal communication with said fluid when said apparatus is positioned within said body lumen, said heat conducting layer being positioned to the inside of said heating device and sensor so as to be in thermal contact with said heating device and said second temperature sensor, said heating device configured to respond to a power signal from said power source to increase a temperature of the heat transfer device to a second temperature above said first temperature.

2. The apparatus of claim 1 wherein said heat conducting layer, said electrically insulated heating device, and said insulating layer form concentric layers, said concentric layers forming a tubular configuration of said heat transfer device.

3. The apparatus of claim 2 wherein said electrically insulated heating device is a high resistance heating filament coiled about said heat conducting layer.

4. The apparatus of claim 2 wherein said heat conducting layer is a copper foil bushing.

5. The apparatus of claim 2 wherein said insulating layer is a biocompatible, hydrophobic polymer.

6. The apparatus of claim 2 wherein said insulating layer and said heat conducting layer are equal lengths and longer than said electrically insulated heating device.

7. The apparatus of claim 6 wherein said insulating layer and said heat conducting layer are from about 0.30 inches to about 0.60 inches in length and said electrically insulated heating device is from about 0.25 inches to about 0.50 inches in length.

8. The apparatus of claim 1 wherein said second temperature sensor comprises a filament thermistor in the form of a coil in contact with said electrically insulated heating device.

9. The apparatus of claim 1 wherein said heat transfer device further comprises a second heat conducting layer positioned between said heating device and said insulating material.

10. A cardiac catheter comprising:
    a catheter support member having a distal end, a proximal end, at least one internal lumen and an outer wall, said catheter support member dimensioned for placement within a body lumen having flowing blood;

a first thermistor for sensing a first blood temperature, said first thermistor positioned along an outer surface of said outer wall;

a second thermistor positioned along said support member and disposed apart from said first thermistor;

a heat transfer device radially disposed about substantially the entire periphery of a segment of said catheter support member outer wall and juxtaposed said second thermistor, said heat transfer device having a generally tubular configuration, said heat transfer device comprising:

an electrically insulated heating layer positioned between a heat conducting layer and a biocompatible material insulating layer, said heat conducting layer in contact with said second thermistor, wherein said heat conducting layer, said biocompatible insulating material layer, and said electrically insulated heating layer are concentric layers forming said tubular configuration, said biocompatible material insulating layer providing electrical insulation for the electrically insulated heating layer, said insulating layer forming an outer layer of said tubular configuration and in contact with said blood when said catheter is placed within a body lumen, said electrically insulated heating layer in thermal communication with the blood when said catheter is placed within said body lumen;

a power supply in electrical communication with said electrically insulated heating layer for supplying electric current to said electrically insulated heating layer, said electrically insulated heating layer responsive to said electric current to increase a temperature of said heat transfer device to a second temperature above said first blood temperature;

a temperature monitor in communication with said first and second thermistors and responsive to said first and second thermistors to ascertain a temperature differential between said first blood temperature and said second temperature;

an electric current control means for controlling said electric current so as to maintain a constant differential between said first blood temperature and said second temperature.

11. The cardiac catheter of claim 10 wherein said catheter support member includes an inflatable balloon positioned at said distal end on said outer wall, said inflatable balloon being in fluid communication with said at least one lumen; and means for inflating said inflatable balloon.

12. The cardiac catheter of claim 11 wherein said at least one lumen comprises a plurality of lumens and wherein said first thermistor, said second thermistor, said electrically insulated heating layer, and said inflatable balloon each have connections in communication with one lumen of said plurality of lumens.

13. The cardiac catheter of claim 10 wherein said cardiac catheter further comprises an electrical wire port at said proximal end, said electrical wire port connected with said at least one lumen.

14. The cardiac catheter of claim 10 wherein said electrically insulated heating layer is a layer formed of a high resistance heating filament of nickel alloy radially disposed in a coiled configuration about said heat conducting layer.

15. The cardiac catheter of claim 10 wherein said heat conducting is a copper bushing having a thickness of from about 0.002 inches to about 0.006 inches and a length of from about 0.3 inches to about 0.6 inches, said copper bushing having an outer plating selected from the group consisting of gold and silver.

16. The cardiac catheter of claim 10 wherein said biocompatible material insulating layer comprises a coating of polyxylylene extending the length of said electrically insulated heating layer and in contact with said electrically insulated heating layer.

17. The cardiac catheter of claim 10 wherein said heat transfer device and said second thermistor are positioned distal to said first thermistor.

18. The cardiac catheter of claim 10 wherein said heat transfer device and said second thermistor are positioned proximal to said first thermistor.

19. A cardiac catheter comprising:

a catheter support member having a distal end, a proximal end, at least one lumen and an outer wall, said catheter support member dimensioned for placement within a body lumen;

a temperature monitor;

a first thermistor configured to sense a first blood temperature, said first thermistor positioned along an outer surface of said outer wall so as to be in thermal contact with said blood when said catheter is placed with said body lumen, said first thermistor in communication with said temperature monitor;

a second thermistor embedded along said outer wall and in communication with said temperature monitor;

a generally tubular heat transfer device radially disposed about the periphery of said outer wall distal to said first thermistor and juxtaposed said second thermistor, said second thermistor configured to sense a second temperature of said tubular heat transfer device, said heat transfer device comprising:

a power supply;

an electrically insulated heating filament in communication with said power supply, said heating filament forming a coil about a heat conductive tubular bushing, said heat conductive tubular bushing being in thermal contact with said second thermistor; and a layer of biocompatible insulating material positioned for contact with said blood when said cardiac catheter is positioned in said body lumen, said layer of biocompatible insulating material being coextensive with said heat conductive tubular bushing and longer than said electrically insulated heating filament so as to provide the electrical insulation between the electrically insulated heating filament and said body lumen;

wherein said heat conductive tubular bushing, said layer of biocompatible insulating material, and said heating filament form concentric layers of said generally tubular heat transfer device.

20. The cardiac catheter of claim 19 wherein said heat conductive tubular bushing is made from copper.

21. The cardiac catheter of claim 19 wherein said electrically insulated heating filament is formed from nickel alloy.

22. The cardiac catheter of claim 19 wherein said layer of biocompatible insulating material is a layer of polyxylylene.

23. A process for monitoring blood volume flow, said process comprising the steps of:

providing a blood volume flow monitor, said monitor comprising:

a cardiac catheter having a distal end, a proximal end, at least one lumen and an outer wall;

a first temperature sensor configured to measure a first blood temperature, said first temperature sensor positioned on an outer surface of said outer wall so as to be in thermal contact with the blood when said cardiac catheter is positioned in a body lumen;

a second temperature sensor embedded along said outer wall displaced from said first temperature sensor;

a heat transfer device positioned apart from said first temperature sensor, radially disposed about said catheter outer wall and juxtaposed said second temperature sensor, said heat transfer device having a generally tubular configuration comprising:

an electrically insulated heating positioned between a heat conducting layer and a biocompatible material layer, said heat conducting layer being in contact with said second temperature sensor, and said biocompatible material layer, said biocompatible material layer forming an outer surface for said heat transfer device so as to electrically insulated said heating layer from said body lumen when said cardiac catheter is positioned within said body lumen, said electrically insulated heating layer in thermal communication with said blood, said electrically insulated heating layer configured to respond to a signal from a power source to increase its temperature to a second temperature above said first blood temperature;

positioning said catheter at a predetermined location within said body lumen having flowing blood, a blood flow direction and said first blood temperature, said blood flow direction being from said proximal end to said distal end;

monitoring said first temperature sensor to determine said first blood temperature;

providing power to said electrically insulated heating layer to provide said second temperature, whereby a temperature differential between said first blood temperature and said second temperature is created;

monitoring said second temperature using said second temperature sensor;

allowing heat to dissipate radially from said electrically insulated heating layer through said biocompatible material layer;

controlling said power to said electrically insulated heating layer to maintain said temperature differential at a constant level, whereby said power to maintain said temperature differential is proportional to blood volume flow; and determining said blood volume flow by monitoring said power to maintain said temperature differential at a constant level.

24. The process of claim 23 wherein said catheter further includes an inflatable device positioned near said distal end and in fluid communication with said lumen and wherein said process further includes the steps of:

inflating said inflatable device to a slidable fit within said body lumen subsequent to providing said catheter;

floating said catheter to said predetermined position within said blood vessel prior to positioning said catheter; and deflating said inflatable device.

25. The process of claim 23 wherein said temperature differential is from about 0.3° C. to about 3° C.

26. The process of claim 23 wherein said body lumen is the pulmonary artery and said blood flow direction is from said proximal end to said distal end.

27. The process of claim 26 including positioning said first temperature sensor proximally to said heat transfer device and said second temperature sensor.

28. The process of claim 23 wherein said blood flow direction is from said distal end to said proximal end and including positioning said heat transfer device and said second temperature sensor proximally to said first temperature sensor.

29. A cardiac output monitor comprising:

a cardiac catheter for placement in a body lumen, said catheter having a catheter body with a distal end, a proximal end, and an outer wall;

a first temperature sensor disposed along said outer wall;

a second temperature sensor embedded along said outer wall apart from said first temperature sensor;

a heat transfer device radially disposed about said outer wall and juxtaposed said second temperature sensor, said heat transfer device comprising:

a power source;

an insulating material forming an outer layer of said heat transfer device;

a heat conducting layer forming an inner layer of said heat transfer device, said heat conducting layer being in contact with said second temperature sensor;

an electrically insulated heating layer positioned between said heat conducting layer and said insulating material, said electrically insulated heating layer in thermal communication with blood in said body lumen, but electrically insulated via said insulating material when said catheter is positioned within a body lumen, said electrically insulated heating layer further in thermal communication with said heat conducting layer, said heating layer in communication with said power source and responsive to a current signal from said power source to increase a temperature of said heat transfer device to a temperature above a temperature of said blood;

means for receiving signals from said first temperature sensor and said second temperature sensor and for determining cardiac output in response to the signals from said first and said second temperature sensors, when said cardiac catheter is positioned within said body lumen.

* * * * *